United States Patent

Zgorzelski et al.

[11] Patent Number: 6,117,277

[45] Date of Patent: *Sep. 12, 2000

[54] PROCESS FOR THE DISTILLATION OF ALCOHOLS

[75] Inventors: Wolfgang Zgorzelski, Oberhausen; Peter Lappe, Dinslaken; Kurt Schalapski, Oberhausen; Wilhelm Gick, Duisburg, all of Germany

[73] Assignee: Celanese Chemicals Europe GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/894,601

[22] PCT Filed: Feb. 14, 1996

[86] PCT No.: PCT/EP96/00633

§ 371 Date: Aug. 22, 1997

§ 102(e) Date: Aug. 22, 1997

[87] PCT Pub. No.: WO96/26173

PCT Pub. Date: Aug. 29, 1996

[30] Foreign Application Priority Data

Feb. 23, 1995 [DE] Germany .......................... 195 06 280

[51] Int. Cl.⁷ ................. B01D 3/34; C07C 27/28
[52] U.S. Cl. ............... 203/37; 568/913; 568/921
[58] Field of Search ................. 203/37, 91, 36, 203/17, 18; 568/913, 921

[56] References Cited

U.S. PATENT DOCUMENTS

| | | |
|---|---|---|
| 2,533,753 | 12/1950 | Ballard et al. . |
| 2,626,284 | 1/1953 | Smith et al. . |
| 2,753,297 | 7/1956 | Mason . |
| 2,889,375 | 6/1959 | Gilbert et al. . |
| 3,359,335 | 12/1967 | Roming et al. . |
| 3,576,891 | 4/1971 | Rosenthal . |
| 3,689,371 | 9/1972 | Kerber et al. . |
| 3,960,672 | 6/1976 | Ester et al. . |
| 3,990,952 | 11/1976 | Katzen et al. ............................. 203/37 |
| 5,312,950 | 5/1994 | Boaz .......................................... 558/51 |

FOREIGN PATENT DOCUMENTS

| | | | |
|---|---|---|---|
| 0142708 | 7/1980 | Germany ................................. 203/37 |
| 253128 | 1/1927 | United Kingdom .................... 202/42 |
| 9515372 | 6/1995 | WIPO . |

OTHER PUBLICATIONS

Chemical Engineering, vol. 2, 3rd ed. Coulson and Richardson, Backhurst and Harker 1978, p. 478.

*Primary Examiner*—Virginia Manoharan
*Attorney, Agent, or Firm*—Connolly, Bove Lodge & Hutz, LLP

[57] ABSTRACT

The invention relates to a process for the purification of $C_3$–$C_{10}$-alcohols by distillation, by distilling the alcohols at 150 to 200° C. in the presence of 10 to 1000 ppm of alkali metal hydroxide.

19 Claims, No Drawings

PROCESS FOR THE DISTILLATION OF ALCOHOLS

This application is the National Phase of international application PCT/EP96/00633, which has an international filing date of Feb. 14, 1996.

Aliphatic $C_3$–$C_{10}$-alcohols, such as n-butanol and, in particular, 2-ethylhexanol, have a high economic importance. These alcohols are preferably prepared by hydroformylation of olefins with subsequent hydrogenation of the aldehydes formed as intermediates (example: propylene→n/i-butyraldehyde→n/i-butanols) or by aldolization of straight-chain aliphatic aldehydes to give the corresponding unsaturated aldehydes and subsequent hydrogenation (example: n-butyraldehyde→2-ethylhexenal→2-ethylhexanol). Summary descriptions are found in, e.g., Ullmann's Encyclopedia of Industrial Chemistry: "Alcohols, Aliphatic" (Vol. A 1), "2-Ethylhexanol" (Vol. A 10) and "Butanols" (Vol. A 4).

Apart from as a solvent, n-butanol is principally used in the paints and coatings sector and for the preparation of carboxylic esters, in particular n-butyl acrylate and di-n-butyl phthalate (DBP).

2-Ethylhexanol is principally required as the alcohol component for the preparation of di-2-ethylhexyl phthalate (DEHP) and 2-ethylhexyl acrylate.

For these fields of application—in particular the preparation of acrylic ester—the use of high-purity alcohols is absolutely necessary. In the industrial preparation of the alcohols, the purification is exclusively performed by multistage fractional distillation. The alcohols in this case are exposed to a thermal stress over a period of several hours, bottom temperatures of 150 to 200° C. being generally employed. As a consequence thereof, in the distillation of aliphatic $C_3$–$C_{10}$-alcohols such as butanol and 2-ethylhexanol, formation of the corresponding aldehydes occurs which can be separated off only with high expenditure under conventional conditions employed in the technique.

The object was therefore to find a simple process for the distillation of $C_3$–$C_{10}$-alcohols which does not have these disadvantages.

Surprisingly, it has been found that addition of small amounts of alkali metal hydroxide suppresses the formation of the corresponding aldehydes during the workup by distillation and aldehydes already present are even eliminated.

The present invention therefore relates to a process for the purification of $C_3$–$C_{10}$-alcohols by distillation, which comprises distilling the alcohols at 150 to 200° C. in the presence of 10 to 1000 ppm of alkali metal hydroxide.

The $C_3$–$C_{10}$-alcohols can be straight-chain or branched. Particularly important $C_3$–$C_{10}$-alcohols, and more preferably $C_4$–$C_{10}$-alcohols to which the process of the invention can be applied are n-butanol and 2-ethylhexanol.

The alkali metal hydroxides used are preferably KOH or NaOH. The amount of alkali metal hydroxide is generally 10 to 1000 ppm, preferably 10 to 200 ppm, in each case based on the amount of the alcohol used. Preferably, the alkali metal hydroxides are added in the form of an aqueous solution.

If columns are used in the distillation, these generally have 20 to 80 trays.

As the following examples show, the addition of alkali metal hydroxide greatly decreases or even completely prevents the formation of aldehydes during the distillation of the alcohols, without other undesirable side reactions or significant reduction of the alcohol content occurring. Frequently, an aldehyde content already present in the alcohol used is even eliminated.

In the examples, the term "low-boilers" refers to components which are free of 2-ethylhexanal and boil considerably lower (at least 20 to 40° C. lower) than 2-ethylhexanol and may therefore readily be separated from this by distillation. Similarly, the term "high-boilers" refers to components which are free of 2-ethylhexanal and boil considerably higher (at least 20 to 40° C. higher) than 2-ethylhexanol and may therefore likewise readily be separated from this by distillation.

COMPARISON EXAMPLE 1

2-Ethylhexanol having a content of 60 ppm (0.006% by weight) of 2-ethylhexanal was heated at 180° C. for 1 hour without addition of alkali metal hydroxide. After 10, 30 and 60 minutes, a sample was taken in each case and analyzed. The results are given in Table 1. After 60 minutes, the 2-ethylhexanal content was 140 ppm (0.014% by weight).

EXAMPLE 1

The procedure was followed as in Comparison Example 1 with the sole exception that 50 ppm of KOH were added to the 2-ethylhexanol before heating was begun. The results are again given in Table 1. After 30 minutes, the 2-ethylhexanal content was already below the analytical detection limit of 0.001% by weight.

TABLE 1

|  | Starting material prior to start | Comparison Example (without alkali metal hydroxide) Time after start | | | Example 1 (50 ppm KOH) Time after start | | |
| --- | --- | --- | --- | --- | --- | --- | --- |
|  | start | 10 min | 30 min | 60 min | 10 min | 30 min | 60 min |
| Low-boilers (% by wt.) | 0.216 | 0.212 | 0.211 | 0.212 | 0.208 | 0.209 | 0.207 |
| 2-Ethylhexanal (% by wt.) | 0.006 | 0.011 | 0.013 | 0.014 | 0.002 | <0.001 | <0.001 |
| 2-Ethylhexanol (% by wt.) | 99.646 | 99.644 | 99.643 | 99.640 | 99.616 | 99.616 | 99.616 |
| High-boilers (% by wt.) | 0.132 | 0.133 | 0.133 | 0.134 | 0.174 | 0.175 | 0.177 |

COMPARISON EXAMPLE 2

663 g of 2-ethylhexanol of the composition below (in % by weight) are used in a 2 l distillation flask in a packed laboratory column having a 1 m high packing of 3 mm VA steel spirals:

| | |
|---|---|
| Low-boilers | 0.099 |
| 2-Ethylhexanal | 0.001 |
| 2-Ethylhexanol | 99.770 |
| High-boilers | 0.130 |

At a column pressure of 100 mbar and a reflux ratio of 3:1, four distillation fractions each of 130 g and a 5th fraction of 65 g were taken off at the column top at a temperature of 118° C. The individual fractions were studied by gas chromatography:

TABLE 2

| Fraction | 1 | 2 | 3 | 4 | 5 |
|---|---|---|---|---|---|
| Low-boilers (% by wt.) | 0.010 | 0.006 | 0.003 | 0.011 | 0.008 |
| 2-Ethylhexanal (% by wt.) | 0.013 | 0.009 | 0.008 | 0.010 | 0.011 |
| 2-Ethylhexanol (% by wt.) | 99.863 | 99.980 | 99.986 | 99.975 | 99.977 |
| High-boilers (% by wt.) | 0.114 | 0.005 | 0.003 | 0.004 | 0.004 |

The 2-ethylhexanal content in the distillation residue (78 g) was below the analytical detection limit.

EXAMPLE 2

The procedure was followed as in Comparison Example 2, with the sole exception that 66 mg of a 50% strength aqueous KOH solution were added to the 2-ethylhexanol before the start of distillation. The individual fractions were again studied by gas chromatography:

TABLE 3

| Fraction | 1 | 2 | 3 | 4 | 5 |
|---|---|---|---|---|---|
| Low-boilers (% by wt.) | 0.010 | 0.006 | 0.003 | 0.011 | 0.008 |
| 2-Ethylhexanal (% by wt.) | 0.003 | 0.002 | 0.001 | 0.001 | 0.001 |
| 2-Ethylhexanol (% by wt.) | 99.863 | 99.987 | 99.993 | 99.984 | 99.987 |
| High-boilers (% by wt.) | 0.124 | 0.005 | 0.003 | 0.004 | 0.004 |

The 2-ethylhexanal content in the distillation residue (78 g) was below the analytical detection limit.

What is claimed is:

1. A process for the purification of a $C_4$–$C_{10}$-alcohol by distillation from a distillation zone, said $C_4$–$C_{10}$-alcohol containing an aldehyde contaminant, said process comprising:

distilling a $C_4$–$C_{10}$-alcohol at 150 to 200° C. in the presence of 10 to 200 ppm of alkali metal hydroxide, recovering from said distillation zone a $C_4$–$C_{10}$-alcohol having a decreased amount of said aldehyde contaminant wherein said alkali metal hydroxide is sodium hydroxide or potassium hydroxide.

2. The process as claimed in claim 1, wherein the $C_4$–$C_{10}$-alcohol in the distillation zone comprises n-butanol.

3. The process as claimed in claim 1, wherein the $C_4$–$C_{10}$-alcohol in the distillation zone comprises 2-ethylhexanol.

4. The process as claimed in claim 1, wherein the alkali metal hydroxide is in aqueous solution.

5. The process as claimed in claim 4, wherein the contents of the distillation zone consist essentially of the $C_4$–$C_{10}$-alcohol and the alkali metal hydroxide.

6. The process as claimed in claim 5, wherein said alkali metal hydroxide is potassium hydroxide.

7. The process as claimed in claim 5, wherein said alkali metal hydroxide is sodium hydroxide.

8. The process as claimed in claim 4, wherein said alkali metal hydroxide is potassium hydroxide.

9. The process as claimed in claim 4, wherein said alkali metal hydroxide is sodium hydroxide.

10. The process as claimed in claim 1, wherein the contents of the distillation zone consist essentially of the $C_4$–$C_{10}$-alcohol and the alkali metal hydroxide.

11. The process as claimed in claim 10, wherein said alkali metal hydroxide is potassium hydroxide.

12. The process as claimed in claim 10, wherein said alkali metal hydroxide is sodium hydroxide.

13. The process as claimed in claim 1, wherein the alkali metal hydroxide suppresses the formation of any additional aldehyde contaminant.

14. The process as claimed in claim 13, wherein said alkali metal hydroxide is potassium hydroxide.

15. The process as claimed in claim 13, wherein said alkali metal hydroxide is sodium hydroxide.

16. The process as claimed in claim 1, wherein said alkali metal hydroxide is potassium hydroxide.

17. The process as claimed in claim 1, wherein said alkali metal hydroxide is sodium hydroxide.

18. A process for the purification of 2-ethylhexanol, containing an aldehyde contaminant, by distillation from a distillation zone, said process comprising:

distilling the 2-ethylhexanol at 150 to 200° C. in the presence of 10 to 200 ppm of potassium hydroxide, and recovering 2-ethylhexanol, containing a decreased amount of said aldehyde contaminant, from said distillation zone.

19. A process for the purification of n-butanol, containing an aldehyde contaminant, by distillation from a distillation zone, said process comprising:

distilling the n-butanol at 150 to 200° C. in the presence of 10 to 200 ppm of potassium hydroxide, and recovering n-butanol, containing a decreased amount of said aldehyde contaminant, from said distillation zone.

* * * * *